United States Patent [19]

Krüger

[11] 4,340,742
[45] Jul. 20, 1982

[54] PROCESS FOR MAKING 5-MERCAPTO-1,2,3-TRIAZOLES

[75] Inventor: Hans-Rudolf Krüger, Berlin, Fed. Rep. of Germany

[73] Assignee: Schering AG, Berlin and Bergkamen, Fed. Rep. of Germany

[21] Appl. No.: 151,110

[22] Filed: May 19, 1980

[30] Foreign Application Priority Data

May 21, 1979 [DE] Fed. Rep. of Germany ........ 2920939

[51] Int. Cl.³ .................. C07D 249/04; C07D 285/06
[52] U.S. Cl. .................................... 548/255; 548/127
[58] Field of Search ............................. 548/127, 255

[56] References Cited

U.S. PATENT DOCUMENTS 4,012,382   3/1977   Bouzard et al. .................... 548/127

OTHER PUBLICATIONS

Smith, Open-chain Nitrogen Compounds, (W. A. Benjamin, Inc., New York, 1965), vol. 1, pp. 69–72, 260–261, 264.
Smith, Open-chain Nitrogen Compounds, (W. A. Benjamin, Inc., New York, 1965), vol. 2, pp. 10–11, 81–84.
Goerdeler et al., Ber. Deut. Chem. Ges., vol. 99, pp. 1618–1631 (1966).
Yale, Chem. Reviews., vol. 33, pp. 242–249 (1943).
Renfrow et al., J. Am. Chem. Soc., vol. 59, pp. 2308–2314 (1937).

*Primary Examiner*—Alton D. Rollins
*Attorney, Agent, or Firm*—Michael J. Striker

[57] ABSTRACT

A process for making 5-mercapto-1,2,3-triazoles of the formula

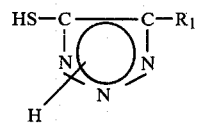

wherein $R_1$ is hydrogen or a $C_1$–$C_4$-alkyl which may also be substituted, the said process comprising
(1) as a first step reacting a solution of 1,2,3-thiadiazole-5-carbohydroxamic acid derivative of the formula

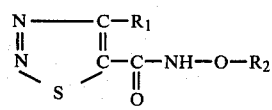

wherein $R_1$ has the meaning as above and $R_2$ is hydrogen or a univalent metal equivalent in an inert organic solvent in the presence of an acid acceptor with a solution in an inert organic solvent of an acid halide of the formula

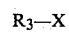

so as to form an acylated 1,2,3-thiadiazole-5-carbohydroxamic acid derivative
(2) reacting as a solution in an inert organic solvent the carbohydroxamic acid derivative just obtained with an alcohol or phenol of the formula

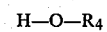

so as to form a (1,2,3-thiadiazole-5-yl)-carbamic acid ester
(3) then treating the thus obtained carbamic acid ester with an acetic or basic catalyst to form the 5-amino-1,2,3-thiadiazole
(4) whereupon the said amino thiadiazole is subject to a rearrangement in the presence of a base followed by isolation of the product of the reaction.

15 Claims, No Drawings

PROCESS FOR MAKING 5-MERCAPTO-1,2,3-TRIAZOLES

BACKGROUND OF THE INVENTION

The invention relates to a process for making 5-mercapto-1,2,3-triazoles which are important starting materials for the production of plant protective agents and pharmaceutical products.

The making of 5-mercapto-1,2,3-triazoles is already known; J. Goerdeler and G. Gnad, Chemische Berichte 99, 1618 (1966).

The process, however, has the serious disadvantage that it uses 5-amino-1,2,3-thiadiazole as starting material which are a class of products which are not of easy access and in addition involve some safety risk.

It is therefore the object of the present invention to provide for a process which permits the making of 5-mercapto-1,2,3-triazoles in only a few steps and with good yields and thus makes possible the industrial production of this class of compounds without isolating any intermediate products which may involve safety risks.

ESSENCE OF THE INVENTION

This object is met by a process for making the 5-mercapto-1,2,3-triazoles of the formula

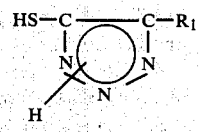

in which $R_1$ may be hydrogen or a $C_1$–$C_4$-alkyl which may also be substituted, the said process comprising the following steps:

(1) As the first step reacting a solution in an inert organic solvent of 1,2,3-thiadiazole-5-carbohydroxamic acid derivative of the formula

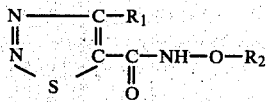

with an acid halide of the formula

     III in the presence of an acid acceptor so as to form an acylated 1,2,3-thiadiazole-5-carbohydroxamic acid derivative of the formula

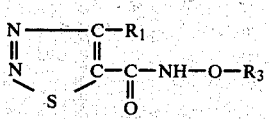

and then (2) reacting the last obtained carbohydroxamic acid derivative with an alcohol or phenol of the formula

     V the reaction carried out in solution in an inert organic solvent to as to form a (1,2,3-thiadiazole-5-yl)-carbamic acid ester of the formula

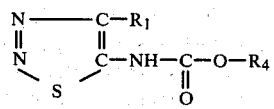

whereupon (3) as a third step this ester is treated with an acidic or basic catalyst to form the 5-amino-1,2,3-thiadiazole of the formula

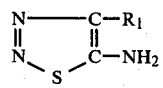

and finally (4) as a fourth step causing a rearrangement of the amino thiazole in the presence of a base whereupon the reaction product of the invention may be isolated in conventional manner.

In all these reactions $R_2$ is hydrogen or a univalent metal equivalent, preferably sodium potassium or lithium, $R_3$ is a $C_1$–$C_4$-alkylcarbonyl which may also be substituted, a $C_1$–$C_4$-alkoxycarbonyl, benzoyl which may also be substituted or an aryl or aryl- or alkylsulfonyl group which may likewise be substituted, $R_4$ is a $C_1$–$C_4$-alkyl, $C_5$–$C_8$-cycloalkyl, an aryl-$C_1$–$C_3$-alkyl which may be substituted, or an aromatic hydrocarbon group which may be substituted in one or several places by $C_1$–$C_6$-alkyl and/or halogen and/or $C_1$–$C_6$-alkoxy and/or nitro and/or trifluoromethyl, X is halogen, preferably chlorine, and $R_1$ has the meaning already above given.

$R_1$ for instance may be hydrogen, methyl, ethyl, propyl, isopropyl, butyl, sec.-butyl, isobutyl, tert.-butyl, chloromethyl, methylthiomethyl or hydroxymethyl.

$R_3$ may be, insofar as the $C_1$–$C_4$-alkylcarbonyl groups are involved, acetyl, propionyl, butyryl, isobutyryl, valeryl, isovaleryl or pivaloyl or, as a substituted $C_1$–$C_4$-alkyl carbonyl group, may be chloroacetyl, dichloroacetyl, trichloroacetyl, methoxyacetyl, 2-chloropropionyl, 3-chloropropionyl, 4-chlorobutyryl, bromoacetyl, 2-bromopropionyl or 3-bromopropionyl. $R_3$ may also be, in respect of the $C_1$–$C_4$ alkoxy carbonyl groups, one of the following: methoxycarbonyl, ethoxycarbonyl, propoxycarbonyl, isopropoxycarbonyl, butoxycarbonyl, tert.-butoxycarbonyl, isobutoxycarbonyl or sec.-butoxycarbonyl; or as substituted benzoyl may be 4-chlorobenzoyl, 3-chlorobenzoyl, 2-chlorobenzoyl, 4-methoxybenzoyl, 3-methoxybenzoyl, 2-methoxybenzoyl, 4-methylbenzoyl, 3-methylbenzoyl, 2-methylbenzoyl or, as aryl or alkylsulfonyl group may be substituted as follows: phenylsulfonyl, 4-tolylsulfonyl, 4-bromophenylsulfonyl, 4-chlorophenylsulfonyl, naphthyl-2-sulfonyl, 4-nitrophenylsulfonyl, 2-nitrophenylsulfonyl, 4-fluorophenylsulfonyl, methylsulfonyl, ethylsulfonyl or benzylsulfonyl.

$R_4$ may for instance be one of the following: alkyl having 1 to 4 carbon atoms, for instance methyl, ethyl, propyl, isopropyl, butyl, sec.-butyl, isobutyl, tert.-butyl, $C_5$–$C_8$-cycloalkyl such as cyclopentyl, cyclohexyl, 2-methylcyclohexyl, 3-methylcyclohexyl, 4-methylcyclohexyl, cycloheptyl, cyclooctyl; aryl-$C_1$–$C_3$-alkyl, for instance benzyl, 4-chlorobenzyl, 2-chlorobenzyl, 4-methylbenzyl, 3-methylbenzyl, 2,4-dichlorobenzyl, 3,4-dichlorobenzyl, 4-methoxybenzyl, α,α-dimethylbenzyl, 1-phenylethyl, 2-phenylethyl, 3-phenylpropyl, 2-phenylpropyl, 1phenylpropyl; an aromatic hydrocarbon group, for instance, phenyl, 4-chlorophenyl, 3-chlorophenyl, 2-chlorophenyl, 2,4-dichlorophenyl, 3,4-dichlorophenyl, pentachlorophenyl, 4-fluorophenyl, 4-methylphenyl, 3-methylphenyl, 2-methylphenyl, 4-nitrophenyl, 3-trifluoromethylphenyl, 4-methoxyphenyl, 3-methoxyphenyl.

PREFERRED EMBODIMENTS AND DETAILS OF THE INVENTION

Preferred embodiments of the process of the invention are the following:

(1) The reaction in the first step of the carbohydroxamic acid derivative of formula II with the acid halide of formula III and the alcohol or the phenol of formula V (step 2) may be carried out at temperatures of $-20°$ to $100°$ C., preferably at temperatures of $0°$ to $50°$ C.

(2) In the steps (2) and (3) the hydroxamic acid derivative of formula II, the acid halide of formula III and the alcohol or phenol of formula V should be reacted in equimolar amounts.

(3) The reaction of the acylated hydroxamic acid derivative of formula IV (which normally is not isolated) with the alcohol or phenol of formula V (step 2) can be carried out in one step.

(4) The reaction of the 1,2,3-thiadiazole-5-carbohydroxamic acid of the formula II with the acid halide of formula III and the alcohol or phenol of formula V (steps I and II) is carried out in one step and the 1,2,3-thiadiazole-5-carbohydroxamic acid of formula II is of a type (formed in known manner) whereby the obtained reaction mixture does not have to be isolated thus permitting a continuous process to be carried out.

(5) The (1,2,3-thiadiazole-5-yl)-carbamic acid ester of the formula VI is of a type that it does not have to be isolated from the reaction mixture, (6) the carbamic acid of formula VI in the reaction catalyzed by a base or acid and carried out at a temperature of $0°$ to $150°$ C., preferably of $50°$ to $120°$ C. is such as to form the 5-amino-1,2,3-thiadiazole of the formula VII which latter compound does not have to be isolated from the solution, and (7) the 5-amino-1,2,3-thiadiazole of the formula VII is of a type that it does not have to be isolated from the reaction mixture, and the 5-amino-1,2,3-thiadiazole of the formula VII is reacted in a process known as such at a temperature of $0°$ to $150°$ C., preferably of $50°$ to $120°$ C. in the presence of a base to form the 5-mercapto-1,2,3-thiazole of the formula I.

THE MAKING OF THE STARTING PRODUCTS

The 1,2,3-thiadiazole-5-carbohydroxamic acids and their salts of the formula II have heretofore not been described in the literature. They have the formula $$\begin{array}{c} N\text{———}C-R_1 \\ \parallel \quad\quad\quad \parallel \\ N \quad\quad C-C-NH-OR_2 \\ \diagdown_S\diagup \quad \parallel \\ \quad\quad\quad O \end{array} \quad\quad II$$

wherein $R_1$ and $R_2$ have the meaning as above indicated. They can be made for instance by the following processes:

A. 1,2,3-thiadiazole carboxylic acid ester of the formula $$\begin{array}{c} N\text{———}C-R_1 \\ \parallel \quad\quad\quad \parallel \\ N \quad\quad C-C-OR_5 \\ \diagdown_S\diagup \quad \parallel \\ \quad\quad\quad O \end{array} \quad\quad VIII$$

are reacted with hydroxylamine of the formula $$H_2N-OH \quad\quad IX$$

if desired in the presence of a suitable inorganic base such as an oxide, a hydroxide or a carbonate or in the presence of an alcoholate of an alkali or alkaline earth metal, and, if desired, in solution in a polar organic solvent.

B. The 1,2,3-thiadiazole-5-carboxylic acid halides of the formula $$\begin{array}{c} N\text{———}C-R_1 \\ \parallel \quad\quad\quad \parallel \\ N \quad\quad C-C-X \\ \diagdown_S\diagup \quad \parallel \\ \quad\quad\quad O \end{array} \quad\quad X$$

are reacted with a hydroxylamine of the formula $$NH_2-OH \quad\quad IX$$

in an inert solvent in the presence of an acid acceptor. $R_5$ in A is a $C_1-C_6$-alkyl residue and $R_1$ and X have the meaning as above indicated.

The process of the invention thus makes use of easily acceptable starting products and permits a technically clear cut and safe production of the desired products.

Of substantial industrial advantage is the fact that neither the acylated carbohydroxamic acid derivative of formula IV, nor the 1,2,3-thiadiazole-5-yl-isocyanate which is formed through the so-called Lossen degradation as intermediate product must be isolated from the reaction mixture. Rather, the reaction can be carried out in a single vessel by directly reacting the carbohydroxamic acid derivative of formula II with the acid halide of formula III (step 1), and the alcohol or phenol of formula V (step 2) in the presence of an acid acceptor.

Of advantage is also that it is possible also to use the crude carbohydroxamic acid or its salts of formula II as well as their crude solution.

A further advantage is that the crude 1,2,3-thiadiazole-5-yl)-carbamic acid ester VI obtained in step 2 as well as their crude solution or suspension can be used for the further reactions.

A particular advantage is furthermore that in the subsequent carbamate hydrolysis the 5-amino-1,2,3-thiadiazole which is not free from safety hazards (formula VII) is formed in step 3 normally only in situ and even then only in solution and does not have to be isolated, but is spontaneously rearranged with alkali to form the 5-mercapto-1,2,3-triazole I (step 4). It was particularly unexpected that by selecting the residue $R_4$ in a proper manner, the carbamate hydrolysis in step 3 could be carried out in an acid or alkali since the carbamates of formula VI form rather stable salts with inorganic bases and on the other hand the compound in formation, the 5-amino-1,2,3-thiadiazole (VII) is considered unstable in the presence of acid.

The reaction of the 1,2,3-thiadiazole-5-carbohydroxamic acid of the formula II, preferably in the form of its crude product so as to form (1,2,3-thiadiazole-5-yl)-carbamic acid ester of formula VI is based on a Lossen-type degradation via the stage of the acylated carbohydroxamic acid of formula IV (step 1) which acylated compound normally does not have to be isolated and that it furthermore proceeds via the stage of the 1,2,3-thiadiazole-5-yl-isocyanate which likewise normally does not have to be isolated, but is formed in situ and reacts immediately with the alcohol or phenol of formula V (step 2).

The reaction is effected at temperatures between −20° and 100° C., preferably between 0° and 50° C.

The reaction can, for instance, be carried out by reacting a crude solution of the hydroxamic acid admixed with an equimolar amount of an acid halide in an inert solution with a mixture of an equimolar amount of alcohol or phenol and an acid acceptor likewise in an inert solvent. This can be done by reacting the hydroxamic acid/acid halide mixture first with the acid acceptor and only then with the alcohol or phenol. For this purpose one reacts first the hydroxamic acid/acid acceptor mixture with the acid halide and only subsequently with the alcohol or phenol. It is also possible to add the acid halide to a mixture of the hydroxamic acid, acid acceptor and alcohol or phenol.

If hydroxamic salts are used it is possible to forego the use of acid acceptors.

As solvents which are inert in respect of the reactants or as suspension agents, the following may be mentioned: aliphatic and aromatic hydrocarbon residues such as cyclohexane, heptane, ligroin, benzene, toluene and xylene; ethers, like diethylether, dioxane, tetrahydrofuran and diisopropylether; esters, like acetic acid ester and malonic ester; ketones, like acetone, methylisobutylketon, isophorone and cyclohexanone; halogenated hydrocarbons, such as methylene chloride, chloroform, chlorobenzene and carbontetrachloride; carboxylic acid amides, such as dimethylformamide and sulfoxides, such as dimethylsulfoxide.

As acid acceptors there may be used organic bases, such as for instance, triethylamine, N,N-dimethylaniline and pyridine bases or inorganic bases such as oxides, hydroxides and carbonates of the earth alkali and alkaline earth metals. Liquid bases such as pyridine can at the same time be used as solvent.

After the reaction has been carried out the reaction mixture is further processed in conventional form, for instance by filtering off the inorganic salts and subsequently distilling off the solvent, at normal or reduced pressure, by precipitation with water or in most cases by merely filtering off the desired reaction product followed by washing out of the inorganic salts with water. In this manner (1,2,3-thiadiazole-5-yl)-carbamic acid ester are obtained at a high purity and in almost quantitative yields and further purification steps are unnecessary. If the reaction is carried out with the crude solutions or crude suspensions a solvent should be used for the Lossen degradation which remains inert also in the subsequent steps. As such are preferred: aromatic hydrocarbons, like benzene, toluene, and xylene; ethers, like tetrahydrofuran and dioxane and halogenated hydrocarbons, such as chloroform, chlorobenzene, 1,2-dichloroethene and methylenechloride.

The saponification of the (1,2,3-thiadiazole-5-yl)-carbamic acid ester can be effected in conventional manner by using an acid as catalyst. In this process it is also possible if desired to isolate the 5-amino-1,2,3-thiadiazole.

For this purpose the carbamate of the formula VI is heated preferably in an aqueous medium and, if desired, in mixture with an inorganic solvent and in the presence of an acid catalyst. The reaction is carried out at temperatures of 0° to 150° C., preferably at temperatures of 50° to 120° C.

As acid catalysts there may be mentioned the following: sulfuric acid, hydrochloric and hydrobromic acid and p-toluene sulfonic acid. As solvents which are inert towards the reactants there may be mentioned: halogenated hydrocarbons, like carbontetrachloride, chloroform, methylene chloride, dichloroethane and chlorobenzene; aliphatic and aromatic hydrocarbons, such as petroleum ether, pentane heptane, cyclohexane, benzene, toluene and xylene; as well as ethers, such as diethylether, tetrahydrofuran and dioxane. Of particular value is the use of carbamates formed by tertiary alcohols because the ease of their saponification by an acid catalyst which is due to the ease of dehydration of tertiary alcohols to olefins. Preferably, the procedure is carried out as follows: the solution or suspension of the tertiary butyl ester is heated in the presence of p-toluene sulfonic acid, solfuric acid or hydrochloric acid so that the corresponding 5-amino-1,2,3-thiadiazole of formula VII is formed upon separation of isobutylene and by way of decarboxylation. The thus formed 5-amino-1,2,3-thiadiazole which is present in solution in an acid aqueous medium is then reacted in the presence of a highly concentrated inorganic base, such as an oxide, hydroxide and carbonate of the alkali or alkali earth metals or also of an alcoholate thereof so as to form the 5-mercapto-1,2,3-triazole of the formula I. Because of the high concentration of the base the 5-mercapto-1,2,3-triazole is present as the corresponding alkali or alkaline earth salt which is isolated only by use of a suitable mineral acid. It is preferred to use the base and the 5-amino-1,2,3-thiadiazole in a molar ratio of 2:1.

The organic solvents which are used during the reaction may also be used as the extraction agents for the 5-mercapto-1,2,3-triazole. After the reaction is complete the extracts are further processed in conventional manner for instance after the necessary drying by distilling off the solvent at normal or reduced pressure. There are thus obtained the 5-mercapto-1,2,3-triazole at a high purity and in very high yields. The reaction time will depend on the reaction temperature and may be between 0.5 and 5 hours.

The saponification of the 5-amino-1,2,3-thiadiazole may also be effected by alkali. It is preferred in that case to heat the carbamate of formula IV, preferably in the form of its crude solution or suspension with an aqueous or alcoholic solution of an alkaline earth hydroxide in a mole ratio of about 1:3 of carbamate to base. The reaction is effected at a temperature of 0° to 150° C., preferably at temperatures of 50° to 120° C. The reaction time depending on the reaction temperature may be between 0.5 and 15 hours. After following this kind of procedure it is not possible to isolate the corresponding 5-amino-1,2,3-thiadiazole but there is obtained directly the alkali salt or alkaline earth salt of the so-called Dimroth rearrangement product. The 5-mercapto-1,2,3-thiadiazoles can then be isolated therefrom in conventional manner.

The following examples will further illustrate the invention:

EXAMPLE 1

Making of 5-mercapto-1,2,3-triazole

In a 500 ml round flask having three inlet tubes and thereby provided with a stirrer, a thermometer and a drying tube there were suspended 14.5 (0.1 mol) of 1,2,3-thiadiazole-5-carbohydroxamic acid in 200 ml tetrahydrofuran and were then reacted at 5° C. with a solution of 19.7 g (0.1 mol) p-toluenesulfonic acid chloride in 50 ml tetrahydrofuran. A mixture of 27.8 ml (0.2 mol) of triethylamine and 9.4 g (0.1 mol) phenol in 75 ml tetrahydrofuran was then added dropwise within the period of 1 hour. The mass temperature was maintained between 4° and 6° C. The mixture was then stirred for 1 hour at 4° C. and for 3 hours at room temperature. The temperature then increased briefly up to 40° C. After standing overnight the mixture was substantially concentrated in a vacuum at 40° C. The residue was reacted with 400 ml ice water. There were obtained white crystals which were removed with suction and were washed first with water and then with toluene.

Yield: 19.2 g of (1,2,3-thiadiazole-5-yl) carbamic acid phenylester)

m.p.: 221° C. (decomposition).

In a similar 500 ml round flask there were heated 19.2 g of the unpurified phenylester just obtained dissolved in 12 g (0.3 mol) sodium hydroxide and 100 ml water for a period of 1.5 hours. The solution was then cooled to 20° C. and reacted with 26.4 ml of concentrated hydrochloric acid. After saturation with 100 g of sodium chloride extraction was effected in batches with 250 ml of acetic acid ester. The acetic ester extracts were shaken with a solution of 20 g of potassium bicarbonate in 75 ml water. The aqueous phase was reacted with 17.6 ml of concentrated hydrochloric acid and was then again reacted in batches with 250 ml of acetic acid.

There were obtained faintly yellow crystals.

Yield: 6.8 g-67.1% of the theoretical amount of 5-mercapto-1,2,3-triazole m.p.: 59° C.

EXAMPLE 2

Making of 5-mercapto-4-methyl-1,2,3-triazole

In the same type of round flask as used in the previous example, 15.9 g (0.1 mol) of 4-methyl-1,2,3-thiadiazole-5-carbohydroxamic acid were suspended in 200 ml tetrahydrofuran and were then reacted with 27.8 ml (0.2 mol) of triethylamine. Subsequently, a solution of 19.1 (0.1 mol) of p-toluenesulfonic acid chloride in 75 ml tetrahydrofuran was added dropwise in a period of 30 minutes. The temperature in the reaction vessel was maintained at between 4° and 6° C. Thereafter, a solution of 9.4 g (0.1 mol) of phenol in 50 ml tetrahydrofuran was added dropwise within 10 minutes and the temperature in the vessel was maintained constant. There followed stirring for 1 hour at 4° C. and for 3 hours at room temperature.

Subsequently, concentration was effected in a vacuum at 40° C. The residue was reacted with 400 ml ice water. There was obtained white crystals which were removed by suction and were washed first with water and then with toluene.

Yield: 12.7 g of (4-methyl-1,2,3-thiadiazole-5-yl)-carbamic acid phenylester m.p.: 153° to 155° C. (decomposition).

In the same kind of round flask there were heated upon reflux 12.7 g of unpurified ester as just obtained in a solution of 12 g (0.3 mol) of sodium hydroxide and 100 ml water during a period of 1.5 hours. The solution was then cooled to 20° C. and reacted with 24.4 ml concentrated hydrochloric acid. After saturation with 100 g sodium chloride, extraction was effected in batches with 250 ml acetic acid ester. The acetic acid ester extracts were shaken with a solution of 20 g potassium bicarbanate in 75 ml water. The aqueous phase was reacted with 17.6 ml concentrated hydrochloric acid and extracted again with 250 ml acetic acid ester. There were obtained slightly yellow colored crystals.

Yield: 6.1 g=53.1% of the theoretical amount of 5-mercapto-4-methyl-1,2,3-triazole m.p.: 113° to 114° C.

EXAMPLE 3

Making of the 1,2,3-thiadiazole-5-carbohydroxamic acid as starting product

In the same round flask as used in the previous examples, 55.6 (0.8 mol) of pulverized hydroxylamine hydrochloride were dissolved in 400 ml methanol and then reacted at 20° C. with a methanolic potassium hydroxide solution formed from 42.0 g (0.75 mol) potassium hydroxide powder and 100 ml methanol. The mass was stirred for 30 minutes at room temperature. It was then removed by suction by the precipitated potassium chloride. The filtrate was reacted in an apparatus as above described at room temperature with 79.1 g (0.5 mol) of 1,2,3-thiadiazole-5-carboxylic acid ethylester. The reaction solution took on immediately a yellow color. After standing for 2 days at room temperature it was concentrated in a vacuum at 40° C. The yellow moist residue was then almost completely dissolved in 300 ml water at 40° C., whereupon carbondioxide was introduced for 45 minutes into the reaction mass at 5° C. The faintly yellow crystals were then removed by suction and were dried in a vacuum at room temperature until a constant weight was obtained.

Yield: 59.6 g=82.1% of the theoretical amount m.p.: 145° C. (decomposition).

EXAMPLE 4

By a method exactly analogous to the method of Example 3 4-methyl-1,2,3-thiadiazole-5-carboxylic acid ethylester was treated to obtain 4-methyl-1,2,3-thiadiazole-5-carbohydroxamic acid which had a melting point of 105° to 110° C. (decomposition). The yield was 86.4% of the theoretical amount.

It is noted specifically that the products made by the process of the invention can be used as the starting products for making various plant protection agents and pharmaceutical compositions.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A process for making 5-mercapto-1,2,3-triazoles of the formula

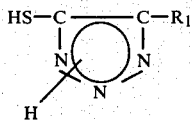

wherein $R_1$ is hydrogen, $C_1$-$C_4$-alkyl or a $C_1$-$C_4$-alkyl substituted by chloro, methylthio or hydroxy, said process comprising (1) as a first step reacting a solution of 1,2,3-thiadiazole-5-carbohydroxamic acid derivative of the formula

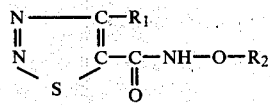

wherein $R_1$ has the meaning as above and $R_2$ is hydrogen or a univalent metal equivalent in an inert organic solvent in the presence of an acid acceptor with a solution in an inert organic solvent of an acid halide of the formula

                            III wherein $R_3$ is $C_1$-$C_4$-alkylcarbonyl, $C_1$-$C_4$-alkylcarbonyl substituted by chloro, dichloro, trichloro, bromo or methoxy, $C_1$-$C_4$-alkoxycarbonyl, benzoyl, benzoyl substituted by chloro, methyl or methoxy, aryl- or alkylsulfonyl or aryl- or alkylsulfonyl substituted by chloro, fluoro, bromo or nitro, and X is halogen, so as to form an acylated 1,2,3-thiadiazole-5-carbohydroxamic acid derivative of the formula

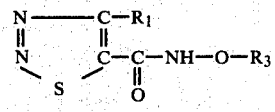

wherein $R_1$ and $R_3$ have the same meaning as above (first step), and (2) reacting as a solution in an inert organic solvent the carbohydroxamic acid derivative just obtained with an alcohol or phenol of the formula

                           V wherein $R_4$ is $C_1$-$C_4$-alkyl, $C_5$-$C_8$-cycloalkyl, aryl-$C_1$-$C_3$-alkyl, aryl-$C_1$-$C_3$-alkyl substituted by chloro, dichloro, methyl, dimethyl or methoxy, or an aromatic hydrocarbon residue which may be substituted in one or several positions by $C_1$-$C_6$-alkyl, halogen, $C_1$-$C_6$-alkoxy, nitro and/or trifluoromethyl so as to form a (1,2,3-thiadiazole-5-yl)-carbamic acid ester of the formula

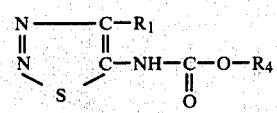

wherein $R_1$ and $R_4$ have the meaning as above (second step), (3) then treating the thus obtained carbamic acid ester with an acidic or basic catalyst to form the 5-amino-1,2,3-thiadiazole of the formula

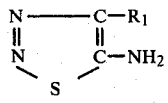

(step 3)

(4) whereupon said amino thiadiazole is not isolated from the reaction mixture and is subject to a rearrangement in the presence of a base followed by isolation of the product of the reaction (step 4).

2. The process of claim 1 wherein the univalent metal equivalent is a sodium, potassium or lithium atom.

3. The process of claim 1 wherein the reaction of the 1,2,3-thiadiazole-5-carbohydroxamic acid derivative of formula II with the acid halide of formula III (step 1) and with the alcohol or phenol of formula V (step 2) is carried out at a temperature of $-20°$ to $100°$ C.

4. The process of claim 3 wherein the reaction is carried out at a temperature between $0°$ and $50°$ C.

5. The process of claim 1 wherein equimolar amounts of the hydroxamic acid derivative of formula II, of the acid halide of formula III and of the alcohol or phenol of formula V are employed in the different reactions.

6. The process of claim 1 wherein the acylated hydroxamic acid derivative of formula IV formed in step 1 is not isolated and wherein the reaction mass formed is in step 2 reacted with the alcohol or phenol of formula V (step 2) in one and the same reaction stage.

7. The process of claim 1 wherein the reaction of the 1,2,3-thiadiazole-5-carbohydroxamic acid of formula II with the acid halide of formula III (step 1) and with the alcohol or phenol of formula V (step 2) is effected in one and the same stage and wherein a 1,2,3-thiadiazole-5-carbohydroxamic acid of the formula II is employed which does not require isolation from the reaction mixture.

8. The process of claim 1 wherein a (1,2,3-thiadiazole-5-yl)-carbaminic acid ester of formula VI is formed in step 2 which does not require isolation from the reaction mixture.

9. The process of claim 1 wherein the carbamic acid ester of the formula VI is subjected to treating with the basic or acidic catalyst (step 3) at a temperature of $0°$ to $150°$ C. to form the 5-amino-1,2,3-thiadiazole of the formula VII which latter does not have to be isolated from the reaction solution.

10. The process of claim 9 wherein said treating with the basic or acidic catalyst is carried out at a temperature between $50°$ and $120°$ C.

11. The process of claim 1 wherein the formed 5-amino-1,2,3-thiadiazole of formula VII (step 3) is not isolated from the reaction mixture and wherein the said 5-amino-1,2,3-thiadiazole is reacted with a base at a temperature between $0°$ and $150°$ C. to form the 5-mercapto-1,2,3-triazole of formula I (step 4).

12. The process of claim 11 wherein said 5-amino-1,2,3-thiadiazole is reacted with a base at a temperature between $50°$ and $120°$ C.

13. A process for making the starting product employed in the reaction of claim 1, said starting product being a 1,2,3-thiadiazole-5-carbohydroxamic acid or a salt thereof of the formula

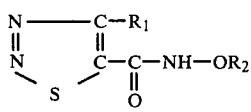

and said process comprising reacting a 1,2,3-thiadiazole-carboxylic acid ester of the formula

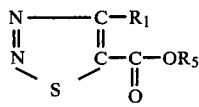

with a hydroxyl amine of the formula

H$_2$N—OH      IX and in the presence of an inorganic base or an alcoholate of an alkali or alkaline earth metal which may be dissolved in a polar organic solvent when R$_2$ is a univalent metal equivalent, R$_2$ and X having the meaning as in claim 1 and R$_5$ being C$_1$-C$_6$-alkyl.

14. A process of making the starting product employed in claim 1 which is a 1,2,3-thiadiazole-5-carbohydroxamic acid or a salt thereof of the formula

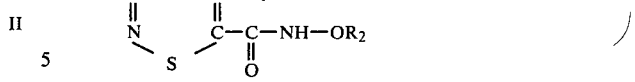

said process comprising reacting a 1,2,3-thiadiazole-5-carboxylic acid halide of the formula

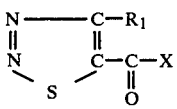

wherein R$_1$ has the meaning as in claim 1 with a hydroxylamine of the formula

H$_2$N—OH      IX

the reaction being carried out in the presence of an inert solvent to which may be added an acid acceptor when R$_2$ is a univalent metal equivalent, R$_2$ having the meaning as in claim 1 and X being a halogen.

15. The process of claim 1 wherein a carbamic acid ester of formula VI wherein R$_4$ is tert.butyl is heated in the presence of p-toluene-sulfonic acid, sulfuric acid or hydrochloric acid whereby isobutylene is separated out and the ester is decarboxylated resulting in the 5-amino-1,2,3-thiadiazole of formula VII in an acidic aqueous medium whereupon the reaction mass is reacted with an inorganic base of an alcoholate of an alkali- or alkaline earth metal, the base being present in the high concentration of 2:1 of base to 5-amino-thiadiazole whereby an alkali- or alkaline earth metal salt of the 5-mercapto-1,2,3-triazole is formed from which the 5-mercapto-1,2,3-triazole is obtained by reaction with a mineral acid.

* * * * *